US00PP32757P2

(12) United States Plant Patent
Pierron-Darbonne

(10) Patent No.: US PP32,757 P2
(45) Date of Patent: Jan. 19, 2021

(54) STRAWBERRY PLANT NAMED 'PLARED 1075'

(50) Latin Name: ***Fragaria* x *ananassa* Duchesne ex Rozier**
Varietal Denomination: Plared 1075

(71) Applicant: Plantas de Navarra, S.A. Sociedad Unipersonal, Valtierra (ES)

(72) Inventor: Alexandre Pierron-Darbonne, Pamplona (ES)

(73) Assignee: Plantas de Navarra, S.A. Sociedad Universal, Navarra (ES)

( * ) Notice: Subject to any disclaimer, the term of this patent is extended or adjusted under 35 U.S.C. 154(b) by 0 days.

(21) Appl. No.: 16/873,361

(22) Filed: Mar. 26, 2020

(30) Foreign Application Priority Data

Jul. 9, 2019 (QZ) ..... PBR 2019/1672

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./156, 208
See application file for complete search history.

*Primary Examiner* — Susan McCormick Ewoldt
*Assistant Examiner* — Karen M Redden
(74) *Attorney, Agent, or Firm* — Knobbe, Martens, Olson and Bear, LLP

(57) ABSTRACT

Described is a new and distinct strawberry variety with varietal denomination 'Plared 1075'. The new variety is characterized by a combination of traits which include, medium vigor plant, upright plant growth habit, and production of medium-size, conical-shaped and firm fruit. 'Plared 1075' is a self-fertile variety.

17 Drawing Sheets

Botanical classification: *Fragaria* x *ananassa* Duchesne ex Rozier.

Variety denomination: The new variety has the varietal denomination 'Plared 1075'.

CROSS-REFERENCE TO RELATED APPLICATIONS

This application claims the benefit of European Community Plant Variety Office Application No. 2019/1672, for a strawberry variety named 'Plared1075', filed on Jul. 9, 2019, the entirety of which is incorporated by reference herein.

BACKGROUND

Disclosed herein is a new and distinct strawberry variety (*Fragaria* x *ananassa* Duchesne ex Rozier). The varietal denomination of the new variety is 'Plared 1075'. The new variety was designated by the breeder as '10.09.214'. The new variety of strawberry was created in a breeding program by crossing two parental varieties in 2010 in Cartaya (Huelva), Spain (about 7° W, 37° N, and 45 feet elevation). The seed parent was an undistributed strawberry variety designated '06-49' (unpatented) and the pollen parent was an undistributed strawberry variety designated '09-024' (unpatented). Each parental variety was a selection from the breeder's program and has not been commercialized.

The resulting seedling of the new variety was grown and asexually propagated by Alexandre Pierron-Darbonne by runners in Segovia, Spain (3° 59'W., 41° 22'N., at 2742 feet elevation) and it was successively propagated by runners first into a screen-house, and afterwards in the fields. Plants of the new variety were further asexually propagated and extensively tested. In order to establish and bring to health the initial head clones, mother plants that had developed several stolons were subjected to a heat treatment, or thermotherapy, at 36° C.-37° C. for 3 to 4 weeks. After that treatment, apical meristems were cut and developed (1 apical meristem corresponding to 1 rooting plant) in an in vitro culture for 5 to 6 weeks. This propagation and testing have demonstrated that the combination of traits disclosed herein which characterize the new variety are retained true to type through successive generations of asexual reproduction.

The growing period in Cartaya (Huelva), Spain (about 7° W, 37° N, and 45 feet elevation), where the observations were made, is between about October 14 and May 20 of the following year, with a date of first flowering of November 20. The observed characteristics are believed to apply to plants grown under similar conditions of soil and climate elsewhere. 'Plared 1075' is a short variety that benefits from induction to flowering by chilling, usually a few hours are sufficient, preferably at temperatures of 7° C. or less. Normally, the minimum number of hours is accumulated in the field over several days.

SUMMARY

Among the characteristics which appear to distinguish the new variety from other varieties are a combination of traits which include inflorescence that appears level with the foliage, slightly larger size of calyx in relation to diameter of fruit, abundant production of medium sized, medium-red colored, conical shaped, and firm fruit, and early time of flowering and ripening. 'Plared 1075' is a not remontant variety.

COMPARISON TO THE PARENTS

The new variety 'Plared 1075' is distinguished from its seed parent '06-49' (unpatented) in that the fruit of the seed parent shows an inserted position of calyx attachment and an attitude of sepals upwards to outwards. In contrast, the attitude of the sepals in the fruit of 'Plared 1075' is outwards and slightly upwards and the calyx attachment is level.

The new variety 'Plared 1075' is distinguished from its pollen parent '09-024' (unpatented) in that the fruit of pollen parent is cylindrical shaped, dark red color, and shows a raised position of calyx attachment and the core is medium red colored. In contrast, the fruit of 'Plared 1075' is conical shaped, medium-red colored, and the core is strong red to moderate reddish orange.

COMPARISON TO CLOSEST VARIETY

The new variety 'Plared 1075' is closest to the variety 'Florida Radiance' (U.S. Plant Pat. No. 20,363) but is distinguished by a number of characteristics.

The leaf of 'Florida Radiance' shows an RHS Green group color near 141 B to 141 A on the upper side, whereas the new variety 'Plared 1075' shows an RHS Green group color near 139 B to 139 A on the upper side.

The terminal leaflet in 'Florida Radiance' shows an obtuse shape of the base, whereas in the new variety 'Plared 1075' the terminal leaflet shows an acute shape of the base.

The margin of the terminal leaflet of 'Florida Radiance' is crenate, whereas the margin of the terminal leaflet of the new variety 'Plared 1075' is serrate to crenate.

'Florida Radiance' shows a red fruit color of RHS Red group near 43 B to 44 C, whereas in 'Plared 1075' the red fruit color is RHS Red group near 44 B to 44 A.

The position of the calyx attachment in the fruit of 'Florida Radiance' is raised, whereas the position of the calyx attachment in the fruit of 'Plared 1075' is level with the fruit.

The attitude of the sepals in the fruit of 'Florida Radiance' is upwards, whereas the attitude of the sepals in the fruit of 'Plared 1075' is outwards and slightly upwards.

The diameter of the calyx in relation to the diameter of the fruit in 'Florida Radiance' is slightly smaller, whereas the diameter of the calyx in relation to the diameter of the fruit in 'Plared 1075' is slightly larger.

The time of beginning of flowering in 'Florida Radiance' is very early, whereas the time of beginning of flowering in 'Plared 1075' is early.

The time of beginning of fruit ripening in 'Florida Radiance' is very early, whereas the time of beginning of fruit ripening in 'Plared 1075' is early.

FIG. 14 shows the differences in the upper side color of the leaf of 'Plared 1075' (designated 10.09.214 in the figure) and 'Florida Radiance'. FIG. 15 shows the differences in the shape of the base in the terminal leaflet and the margin of the terminal leaflet of 'Plared 1075' (designated 10.09.214 in the figure) and 'Florida Radiance'. The differences in the fruit color, position of the calyx attachment, the attitude of sepals and the diameter of the calyx in relation to the diameter of the fruit are shown in FIG. 16 and FIG. 17. These differences are maintained during the harvest season.

BRIEF DESCRIPTION OF PHOTOGRAPHS

The accompanying photographs show typical specimens of the new variety, designated 10.09.214 in the illustrations, including fruit, foliage and flower, in color as nearly true as it is reasonably possible to make in color illustrations of this character.

The plants depicted in the drawings were planted October 14 at the farm of La Mogalla in Cartaya (Huelva), Spain, about 7° W, 37° N, 45 feet elevation.

Photographs were taken March-April (about March 25 and April 25) when there was a minimum temperature of about 10 to 12° C. and a maximum temperature of about 22 to 24° C.

Figure 1:
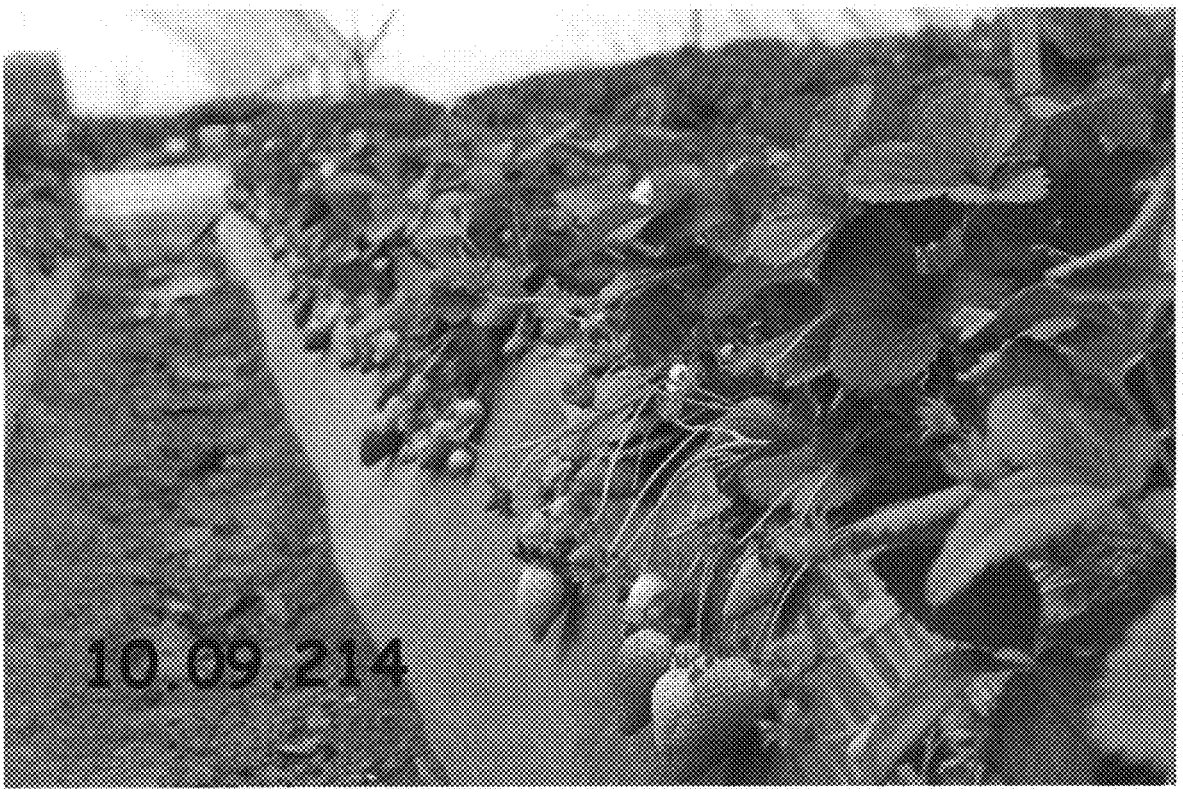
FIG. 1 shows several plants of the new variety with several medium red colored and conical shape fruits.
Figure 2:
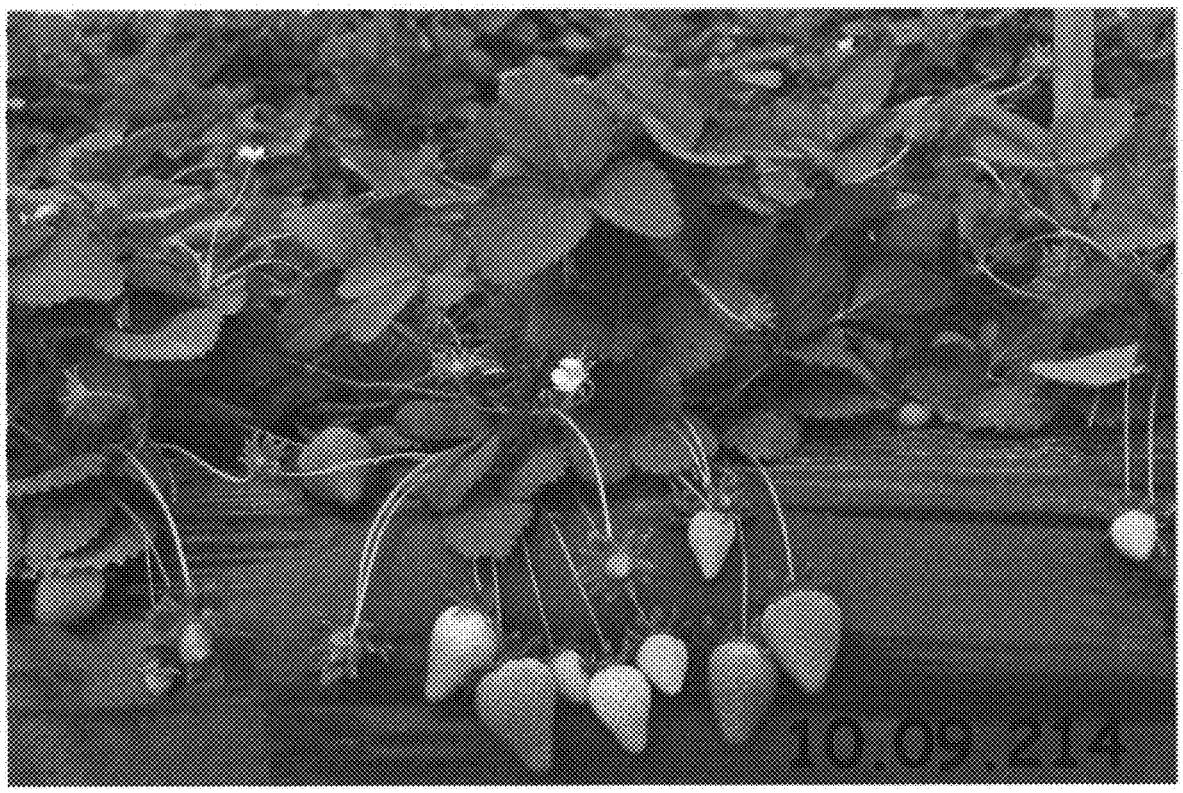
FIG. 2 shows several plants of the new variety which exhibit an upright habit, a medium density plant and the position of the inflorescence relative to foliage at the same level.
Figure 3:
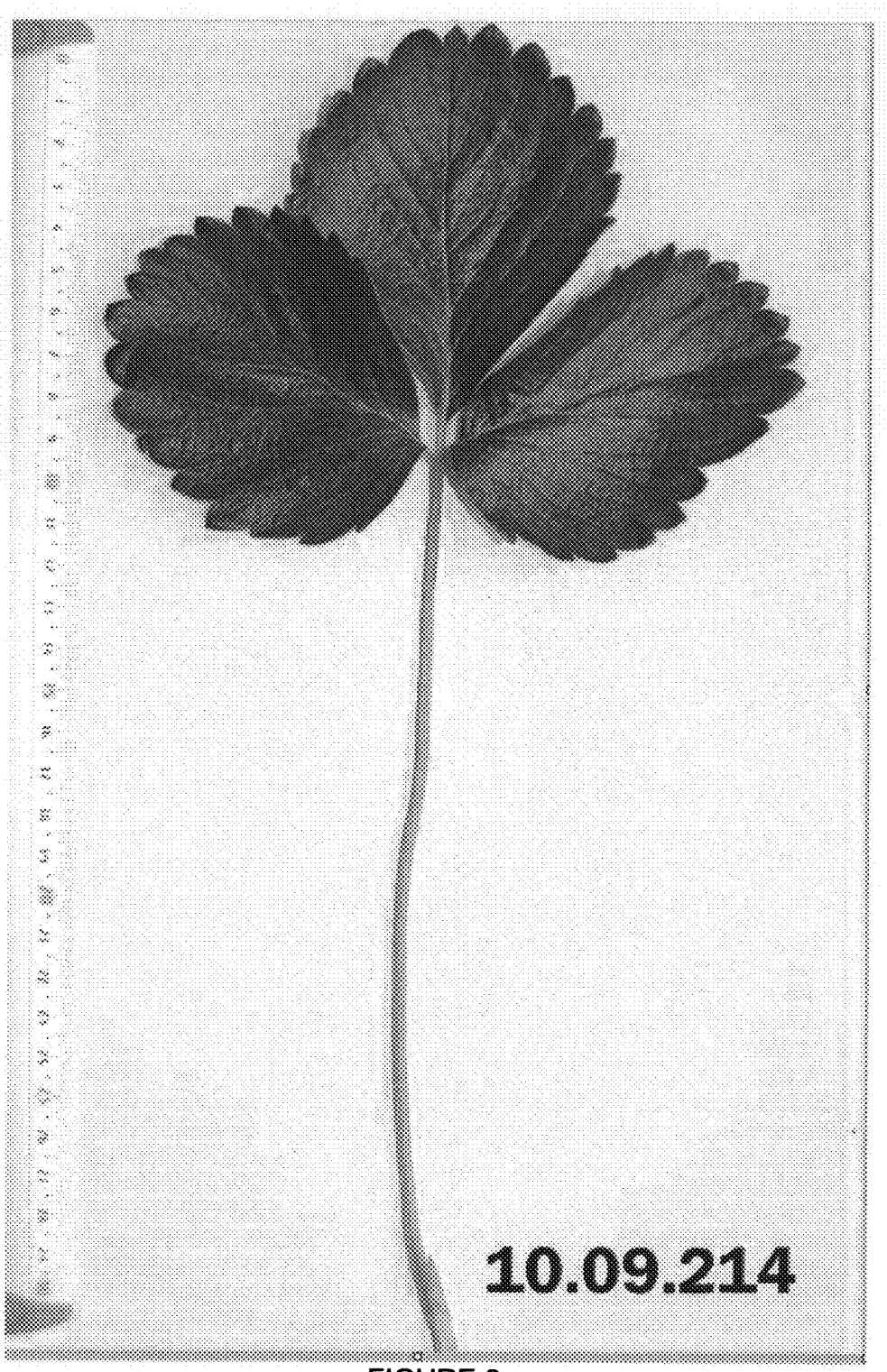
FIG. 3 shows the upper side of a complete leaf of the new variety. In it we can see that the leaf color of upper side is RHS Green group color near 139 B to 139 A.
Figure 4:
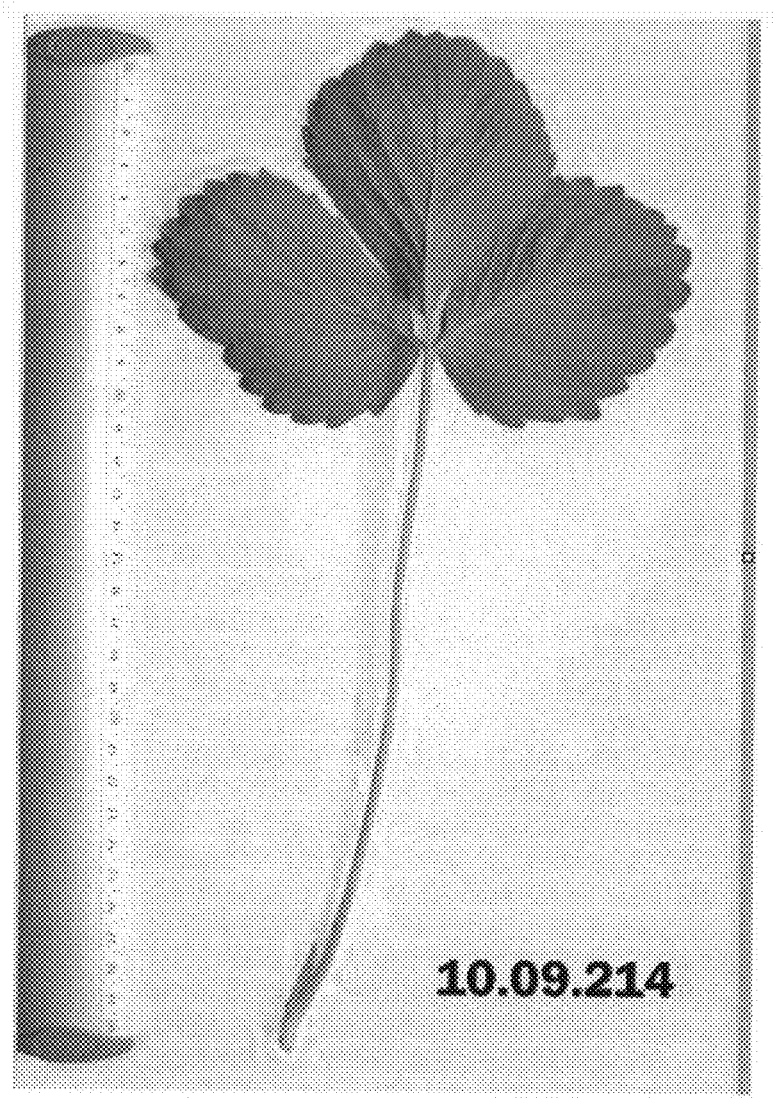
FIG. 4 shows the underside of a complete leaf of the new variety. The leaf color of underside is RHS Yellow-Green group color near 144 A to 146 D.
Figure 5:
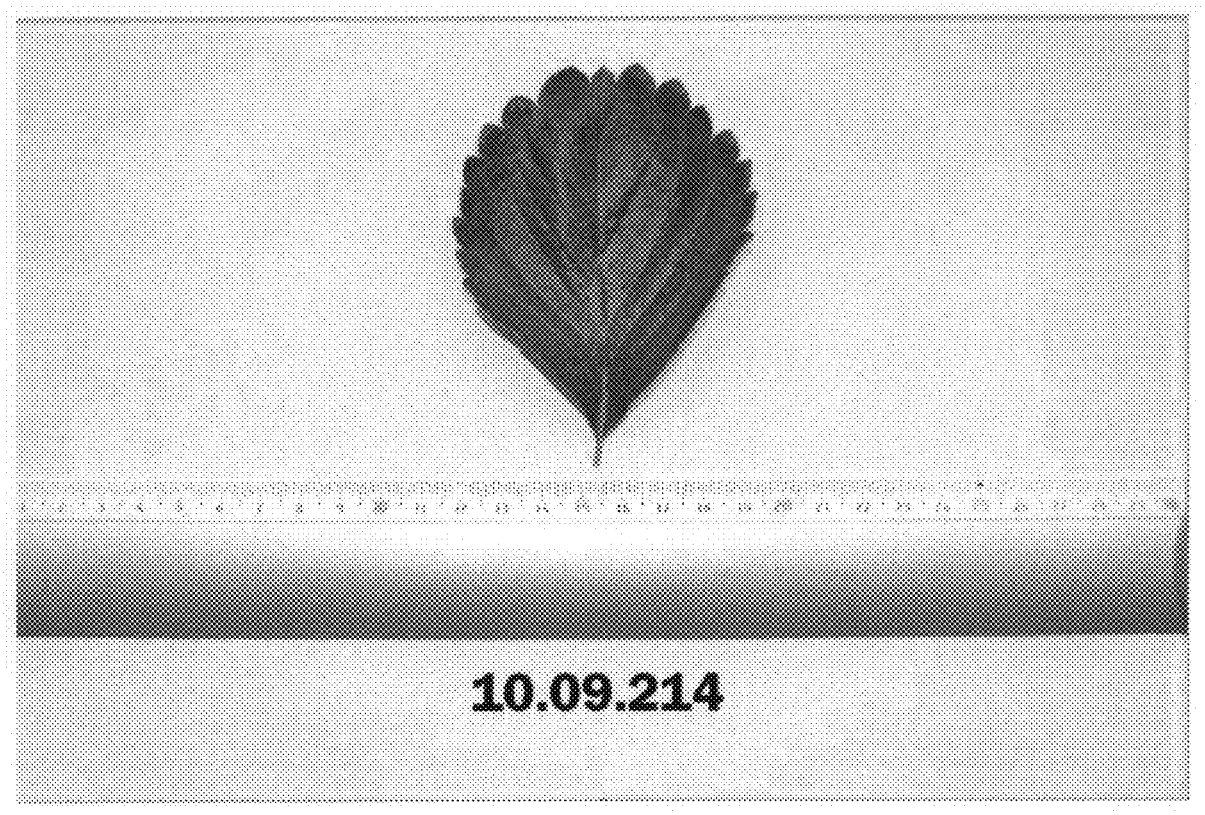
FIG. 5 and FIG. 6 show the upper side and the underside, respectively, of the terminal leaflet of the new variety. The acute shape of the base can be observed.
Figure 6:
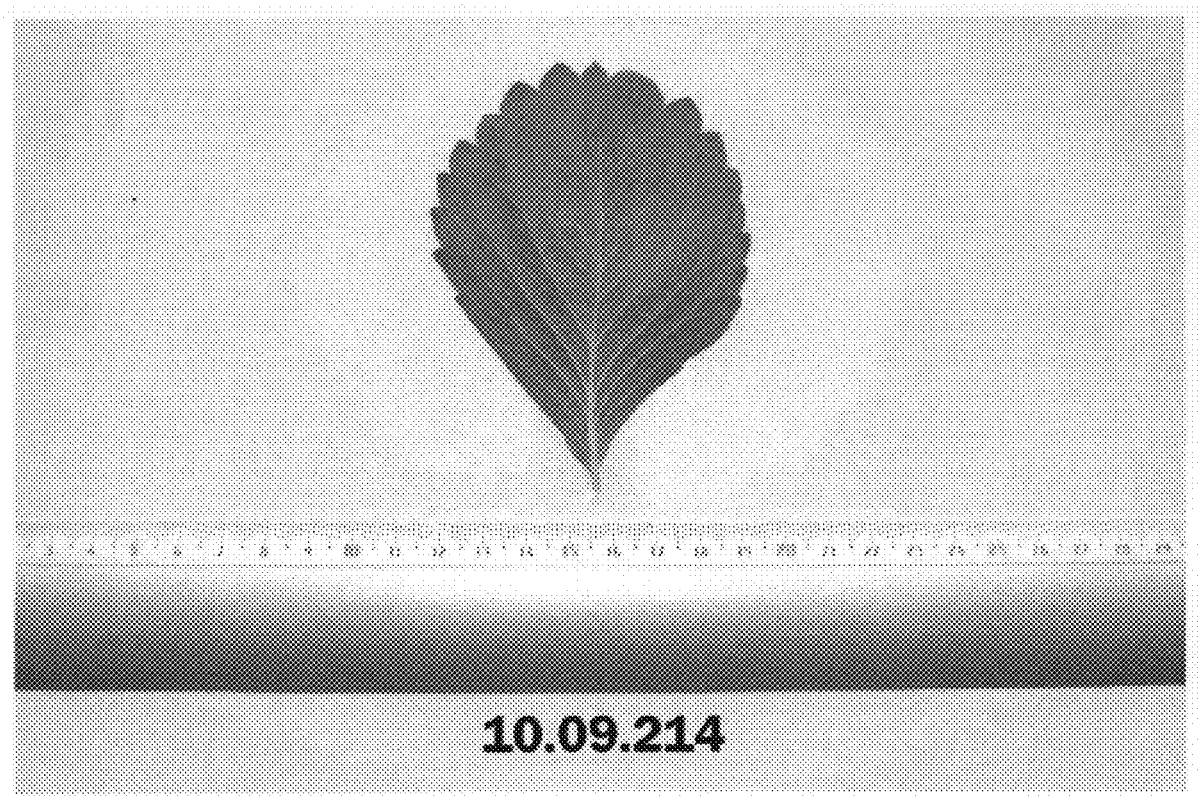
Figure 7:
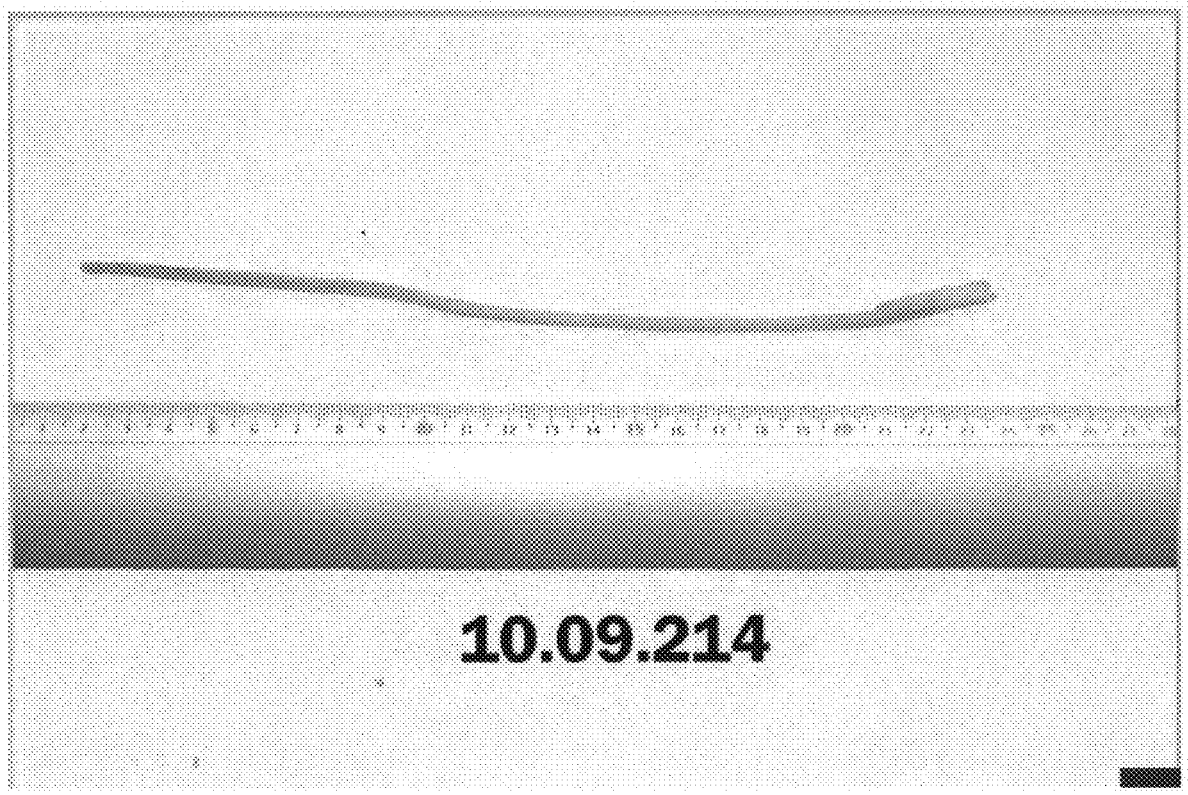
FIG. 7 show the stipule of the new variety with an anthocyanin coloration absent or very weak, with a RHS Yellow-Green group coloration near 145 D to 145 C.
Figure 8:
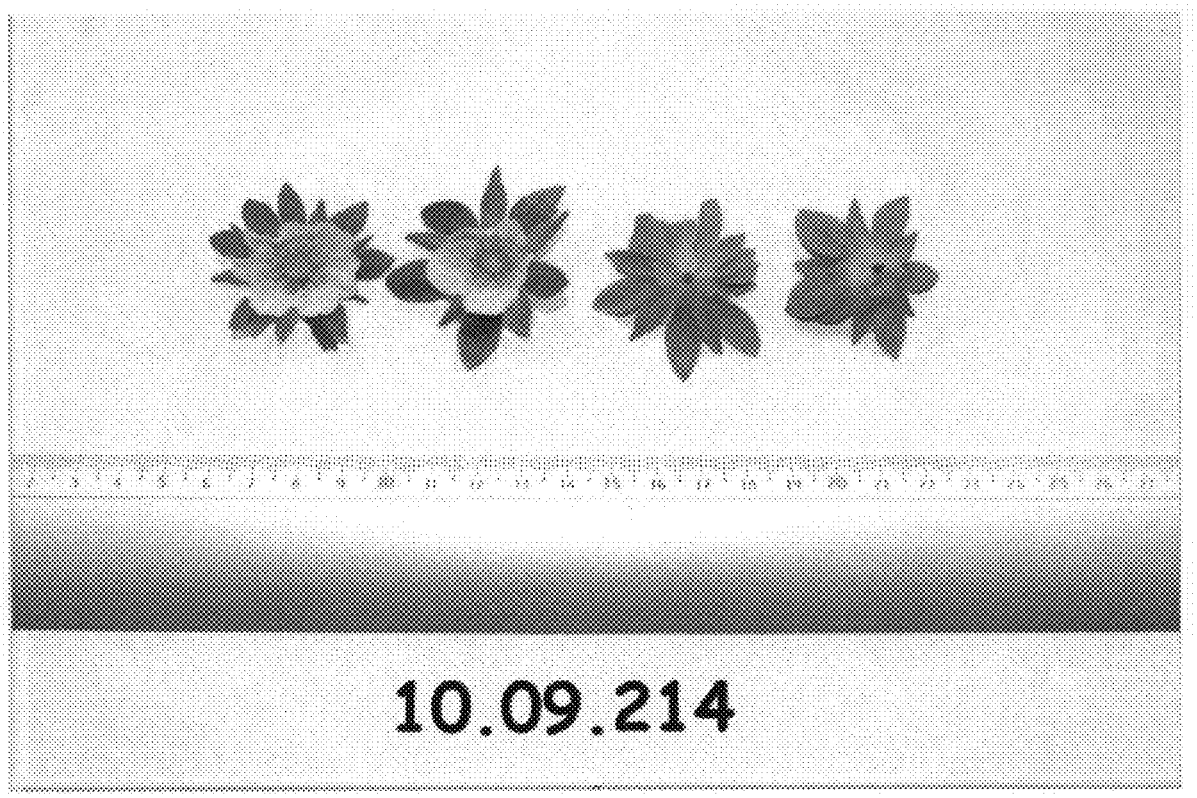
FIG. 8 shows several flowers of the new variety.
Figure 9:
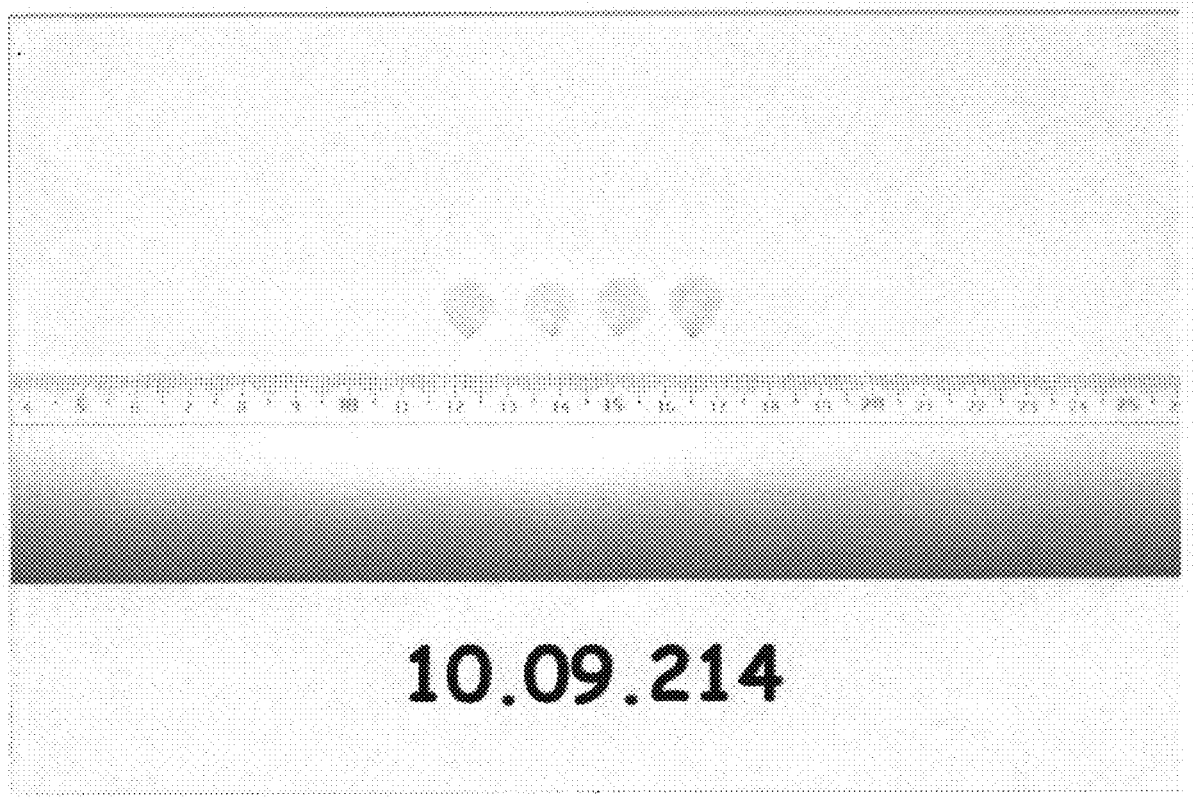
FIG. 9 shows several petals of the new variety: the upper side is represented by the two on the left, and the underside is represented by the two on the right.
Figure 10:
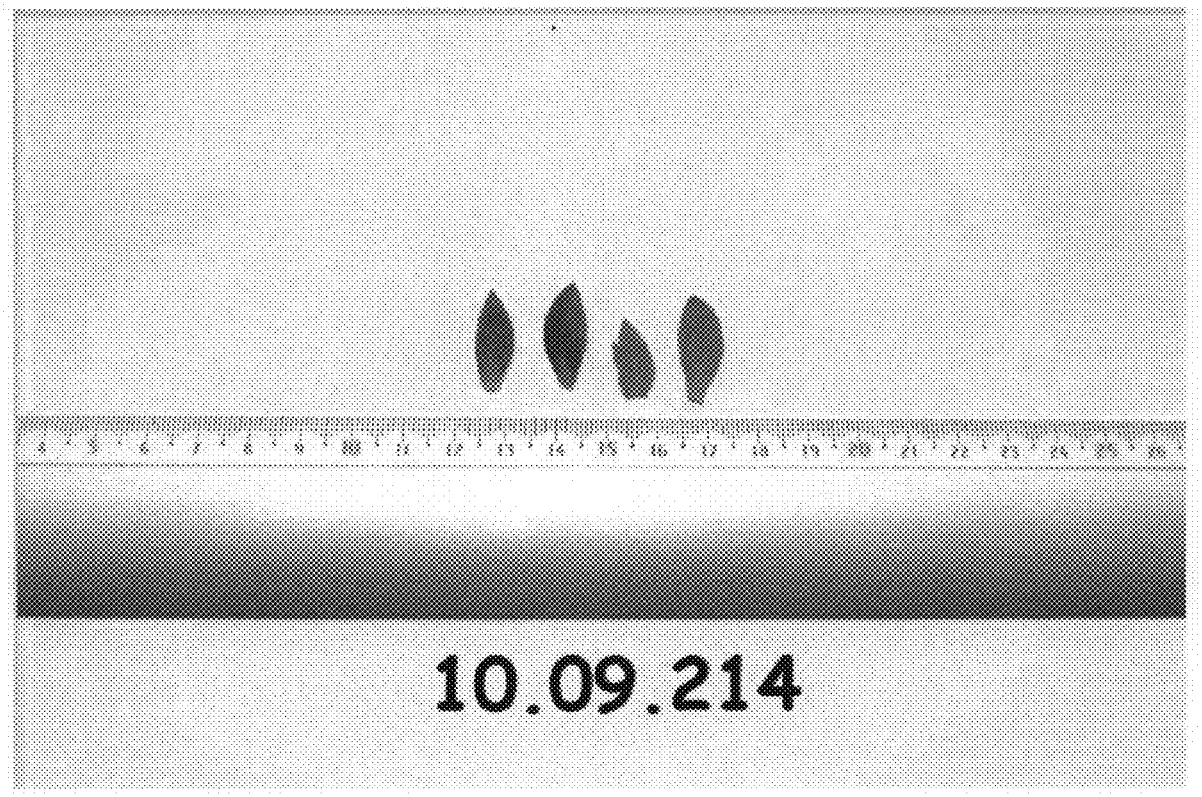
FIG. 10 shows upper side and underside of typical sepals of the new variety. The upper side is represented by the two on the left, with a RHS Green group color near 141 B to 141 A, and the underside is represented by the two on the right, with a RHS Yellow-Green group color near 143 B to 143 A.
Figure 11:
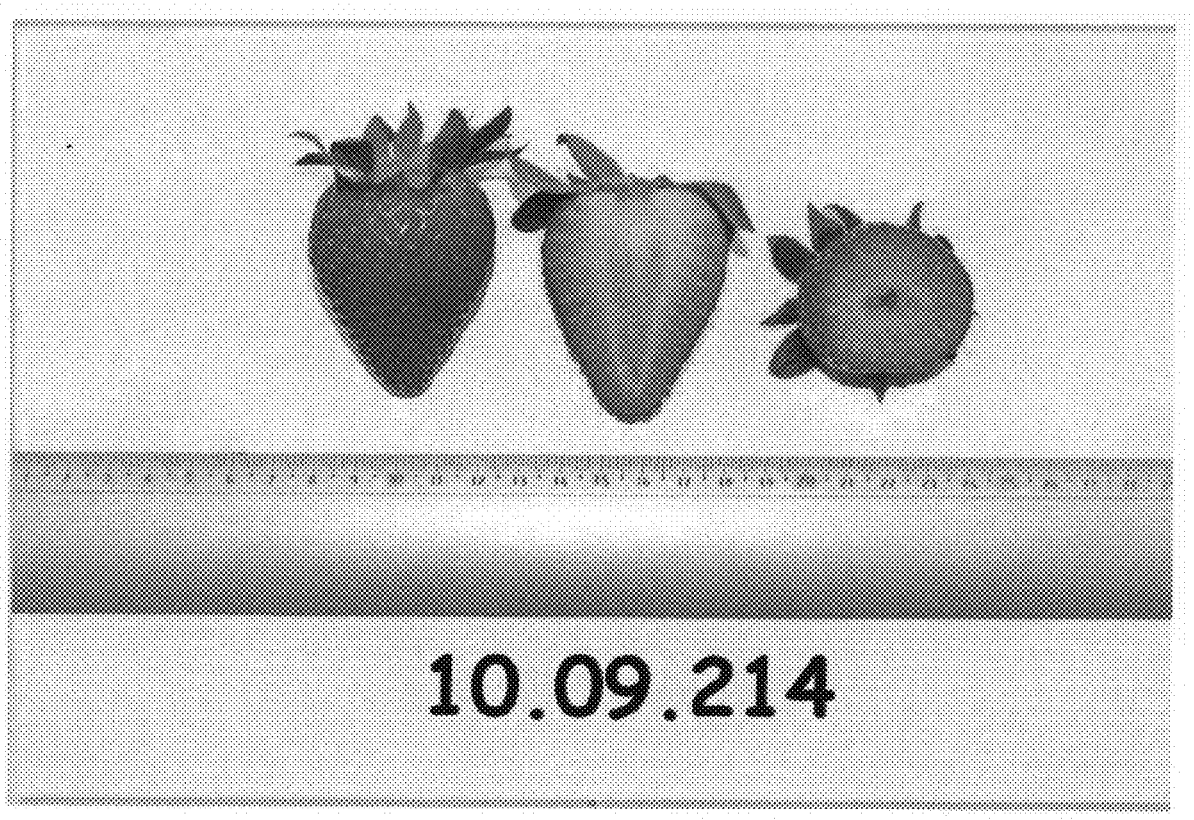
FIG. 11 shows typical fruit of the new variety whole, sliced and in cross section, illustrating the typical medium red fruit color (RHS Red group near 44 B to 44 A), the typical medium red flesh coloration (RHS Red group near 43 B to 44 C), lightening toward center, with an absent or small hollow center.
Figure 12:
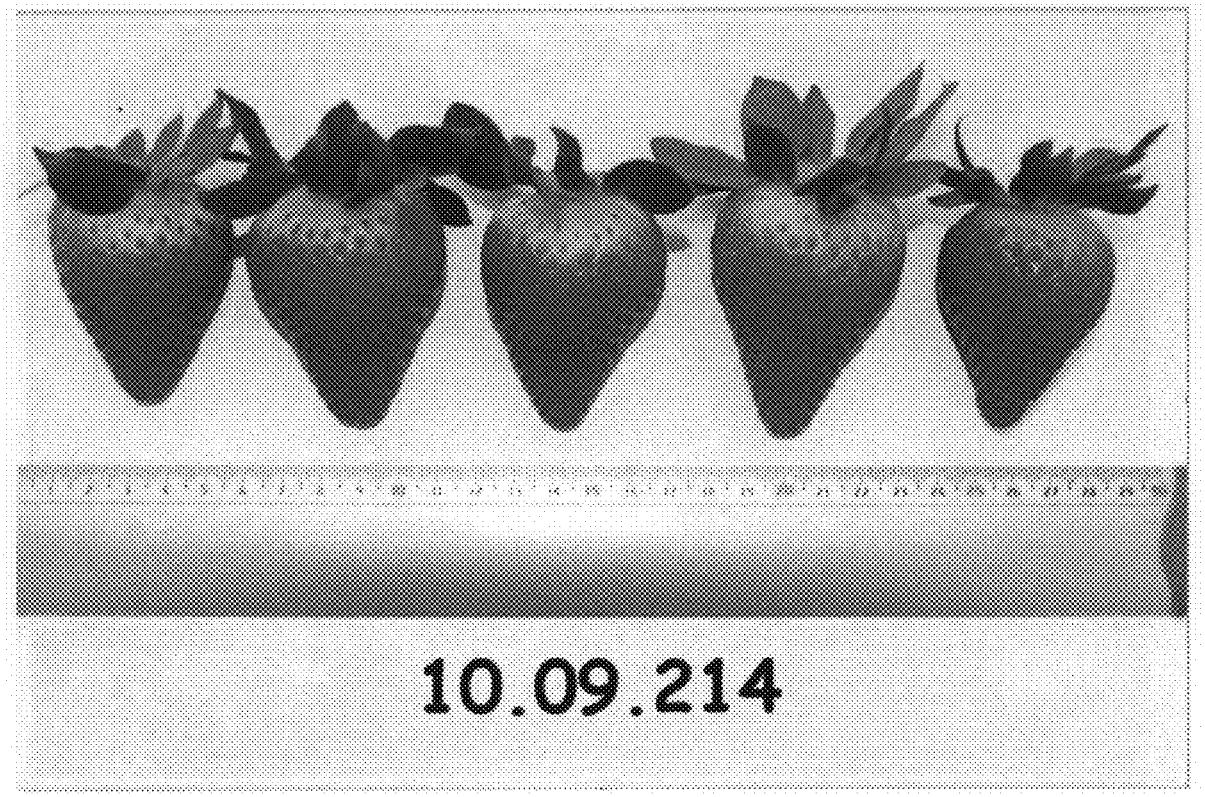
FIG. 12 shows several typical fruits of the new variety illustrating the typical conical shape and medium red fruit color (RHS Red group near 44 B to 44 A).
Figure 13:
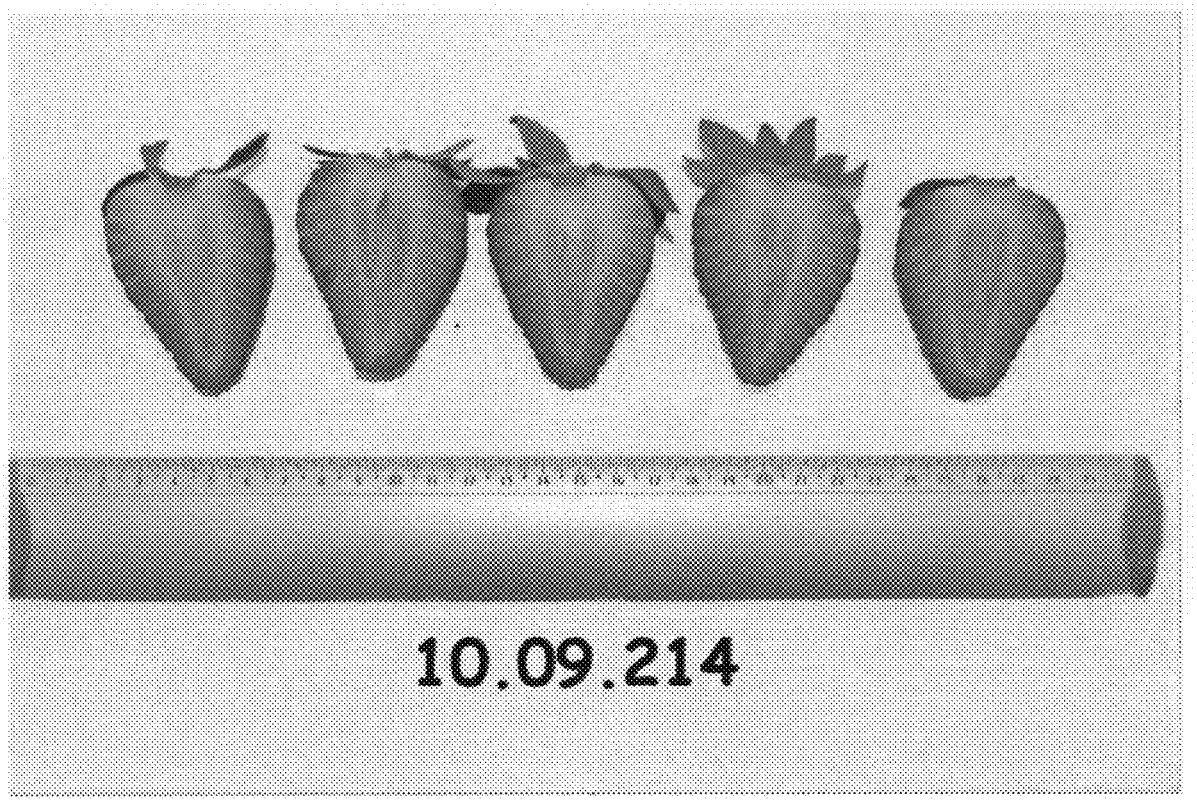
FIG. 13 shows several typical fruits of the new variety in cross section illustrating the typical medium red flesh coloration (RHS Red group near 43 B to 44 C), lightening toward center, with an absent or small hollow center.
Figure 14:
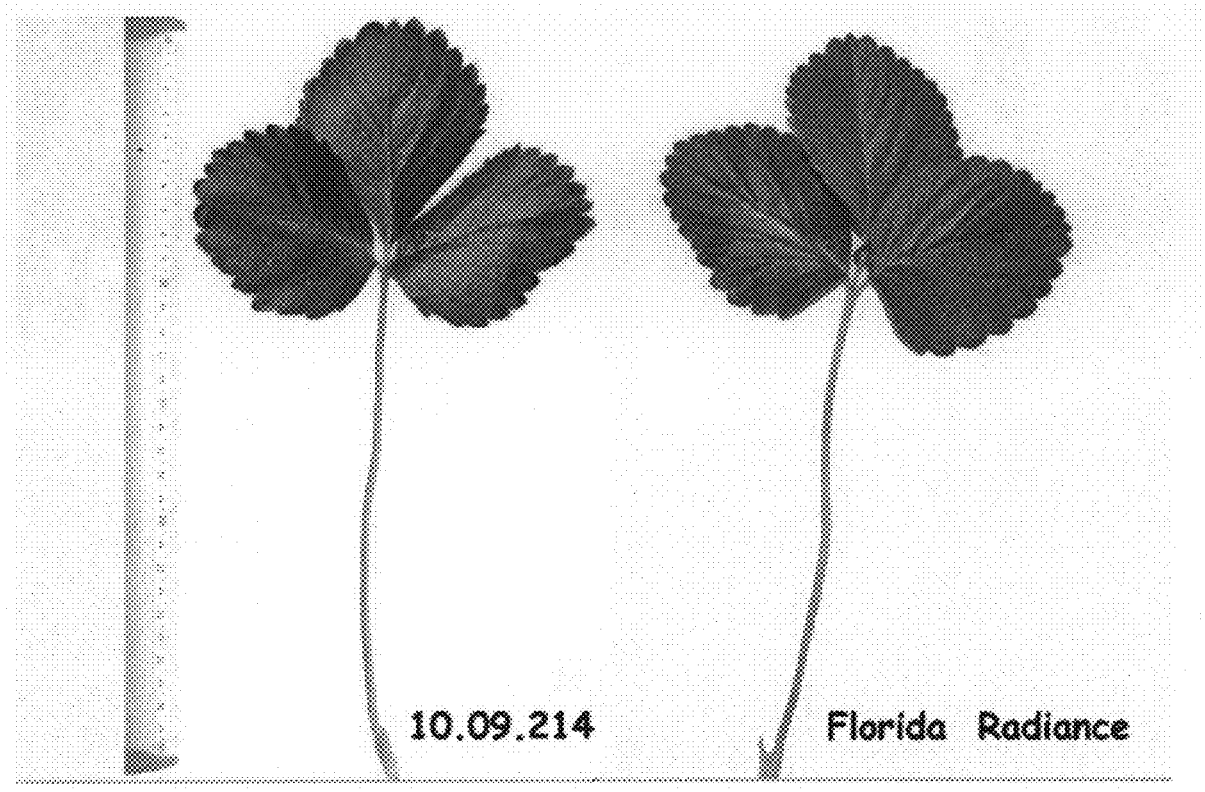

FIG. 14 shows a comparison between the complete leaf of the new variety and the strawberry variety 'Florida Radiance'. In it we can see that leaf of 'Florida Radiance' shows an RHS Green group color on the upper side near 141 B to 141 A, whereas the new variety (designated 10.09.214 in the figure) shows a RHS Green group color in the upper side near 139 B to 139 A.

Figure 15:
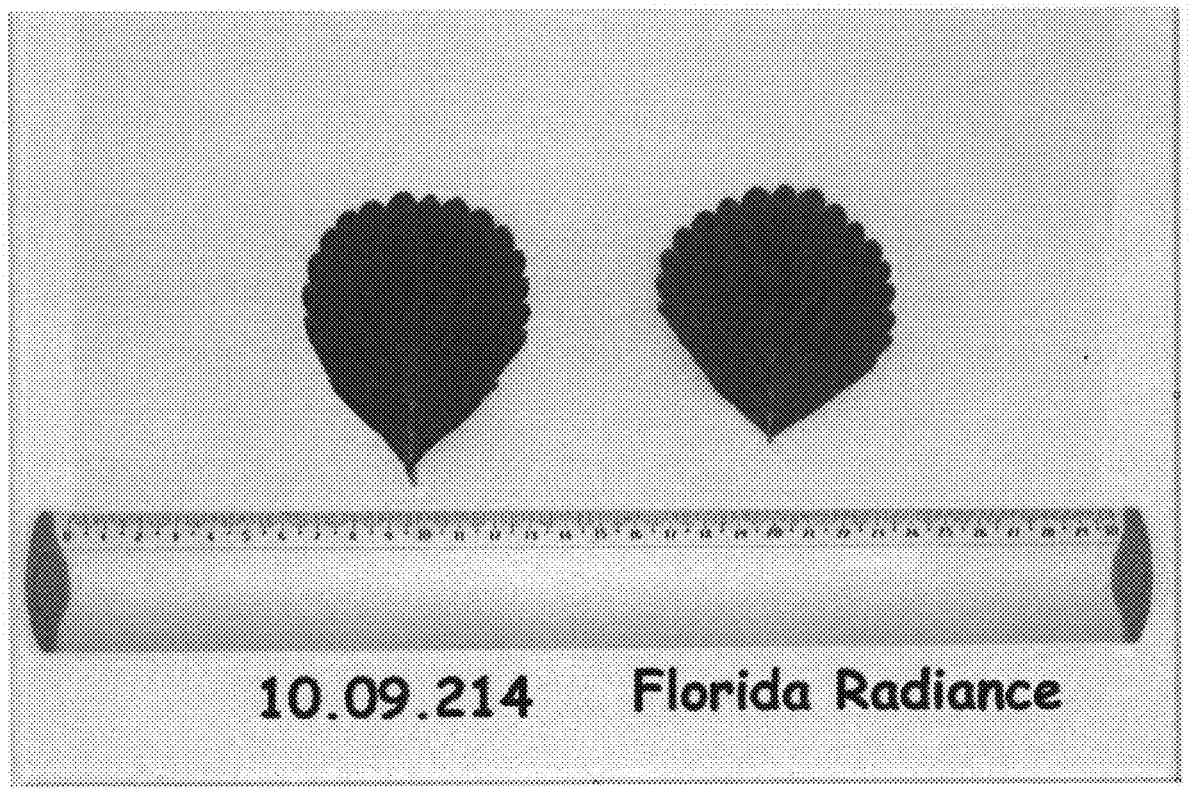

FIG. 15 shows a comparison between the terminal leaflet of the new variety (designated 10.09.214 in the figure) and the strawberry variety 'Florida Radiance'. In it we can see that the terminal leaflet in 'Florida Radiance' shows an obtuse shape of the base, whereas in the new variety (designated 10.09.214 in the figure) the terminal leaflet shows an acute shape of the base.

Figure 16:
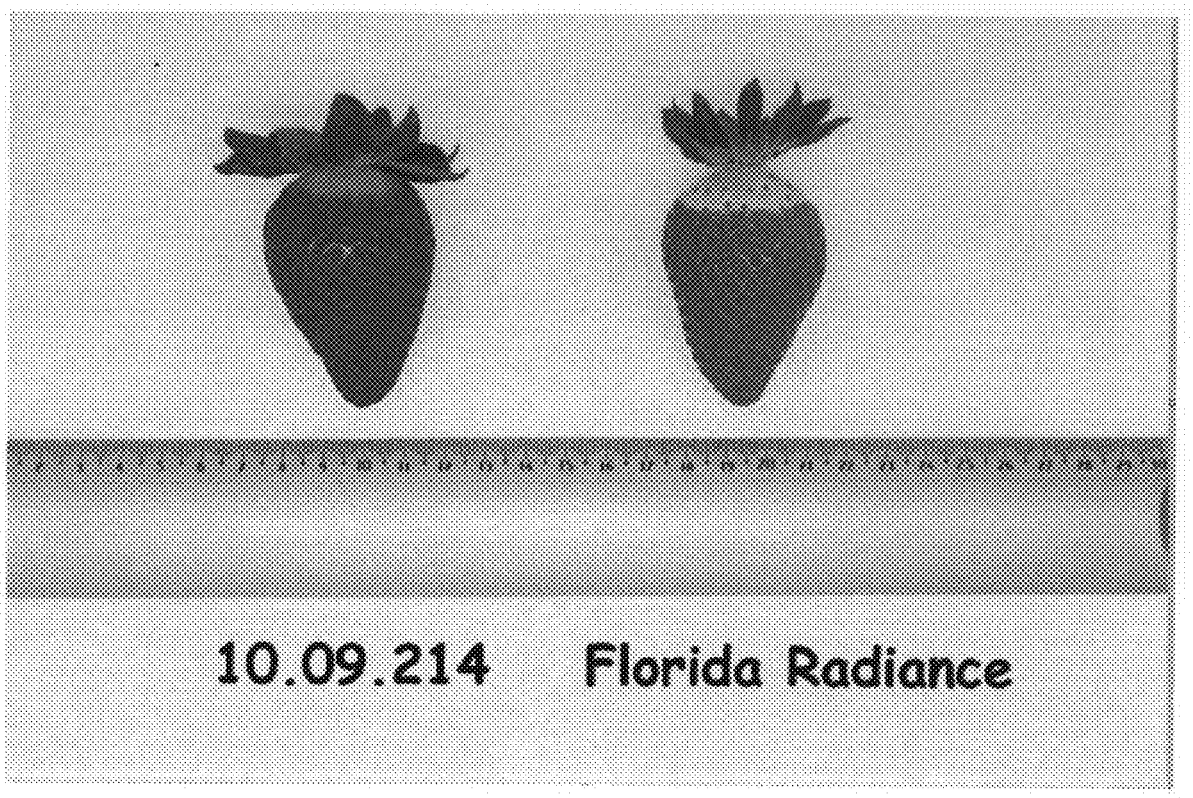
Figure 17:
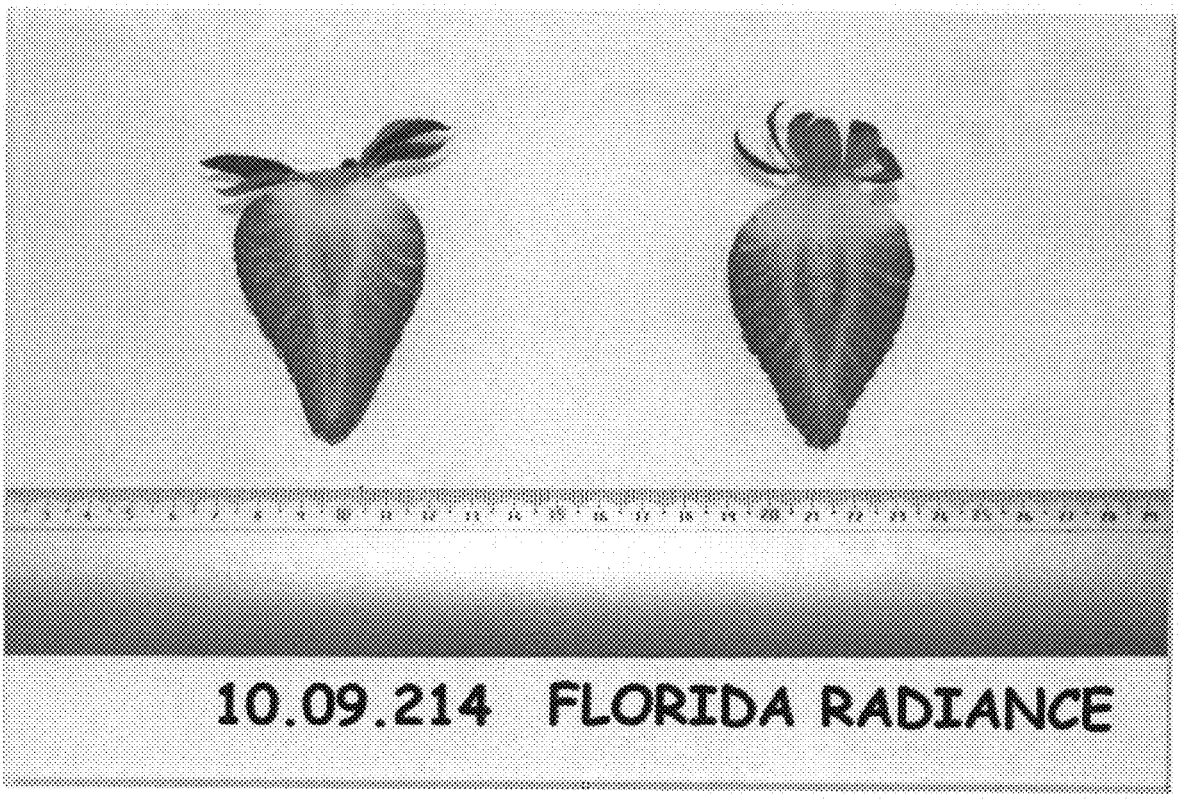

FIG. 16 and FIG. 17 show the comparison between fruits of the new variety (designated 10.09.214 in the figure) and the strawberry variety 'Florida Radiance'. In FIG. 16 and FIG. 17 we can see that in 'Florida Radiance' the diameter of the calyx in relation to the diameter of the fruit is slightly smaller, shows a red fruit color (RHS Red group near 43 B to 44 C), position of calyx attachment in the fruit is raised and the attitude of the sepals is upwards. In contrast, in the new variety (designated 10.09.214 in the figures) the diameter of the calyx in relation to the diameter of the fruit is slightly larger, shows a red fruit color (RHS Red group near 44 B to 44 A), the position of the calyx attachment in the fruit is level with fruit and the attitude of the sepals is outwards and slightly upwards.

DESCRIPTION OF THE NEW VARIETY

Throughout this specification, color names beginning with a small letter signify that the name of that color, as used in common speech is apply descriptive. Color names beginning with capital letter designate values based upon The R.H.S. Colour Chart published by The Royal Horticultural society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown under tunnel at the farm La Mogalla, in Cartaya (Huelva), Spain (7° W., 37° N., 45 feet elevation). Plants were planted on October 14 with a sample size of two repetitions and 250 plants per repetition. After planting, plants were grown under tunnels in raised beds covered with plastic and with small holes in plastic walls. Water and fertilizer were applied trough drip irrigation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface undulation inherent to leaves and is generally a constant characteristic.

'Plared 1075' is a short day variety that needs an induction to flowering by chilling, such as occurs at a high elevation nursery (fresh plant) or with cold storage (referred to as a frigo plant). Usually a short time (several hours) is sufficient. 'Plared 1075' is self-fertile. It produces large quantities of pollen throughout the season and pollination is generally good as there are very few malformed fruit.

TABLE 1

Table 1 shows the accumulated production of Commercial Quality Fruit (g/plant) of the new variety 'Plared 1075' when compared to its varieties 'Florida Radiance' (U.S. Plant Pat. No. 20,363) and 'Planasa 0955' (U.S. Plant Pat. No. 30,542) during the months of February, March, April and May.

| Variety | 28-Fb | 31-Mr | 30-Ap | 20-My |
|---|---|---|---|---|
| Plared 1075 | 135 | 368 | 778 | 928 |
| Florida Radiance | 143 | 350 | 729 | 890 |
| Planasa 0955 | 96 | 388 | 826 | 1073 |

TABLE 2

Table 2 shows the Total Yield from October 14 to May 20 and fruit weight average of the new variety 'Plared 1075' when compared to varieties 'Florida Radiance' and 'Planasa 0955'.

| Variety | $1^{st} + 2^{nd}$ Quality Fruit | Total | Weight (g/fruit) |
|---|---|---|---|
| Plared 1075 | 928 + 139 | 1067 | 26-24 |
| Florida Radiance | 890 + 151 | 1041 | 27-24 |
| Planasa 0955 | 1073 + 165 | 1238 | 27-25 |

TABLE 3

TABLE 3 shows the Production Total, to May 20 of First Quality Fruit ($1^{st}$ quality) and Second Quality Fruit ($2^{nd}$ quality) in g/plant, of the new variety 'Plared 1075' when compared to its varieties 'Florida Radiance' and 'Planasa 0955'.

| Variety | $1^{st}$ quality | $2^{nd}$ quality | TOTAL ($1^{st}$ quality + $2^{nd}$ quality) | $2^{nd}$ quality |
|---|---|---|---|---|
| Plared 1075 | 928 | 139 | 1067 | 13.0 |
| Florida Radiance | 890 | 151 | 1041 | 14.5 |
| Planasa 0955 | 1073 | 165 | 1238 | 13.3 |

$$\% \ 2^{nd} \text{ quality} = \frac{2^{nd} \text{ quality}}{\text{TOTAL}} \times 100$$

TABLE 4

Table 4 shows the Weight (g/fruit) at two dates: March 31 and May 20 of the new variety 'Plared 1075' when compared to varieties 'Florida Radiance' and 'Planasa 0955'.

| WEIGHT (g/fruit) | 30 March | 11 May |
|---|---|---|
| Plared 1075 | 26 | 24 |
| Florida Radiance | 27 | 24 |
| Planasa 0955 | 27 | 25 |

WEIGHT is shown as the average weight per fruit in First Quality Fruits.

TABLE 5

Table 5 shows a comparison of the fruit analysis between the new variety 'Plared 1075' and varieties 'Florida Radiance' and 'Planasa 0955'.

FRUIT ANALYSIS

| | Florida Radiance | Plared 1075 (10.09.214) | Planasa 0955 |
|---|---|---|---|
| Firmness (Kg) | 0.60 | 0.60 | 0.60 |
| Humidity & Volatile Matter (%) | 91.30 | 92.50 | 93.00 |
| Dry Matter (%) | 8.70 | 7.50 | 7.00 |
| PH (to 20°) | 3.70 | 3.60 | 3.50 |
| Acidity as Anhydride Citric (%) | 0.56 | 0.55 | 0.57 |
| Soluble Solids (°Brix) | 7.70 | 7.50 | 7.60 |
| Maturity Index | 13.80 | 13.60 | 13.30 |
| Content in Ascorbic Acid (ppm) | 22.20 | 22.60 | 20.60 |
| Dominant Tonality (nm) | 490 | 500 | 505 |
| Luminosity: | | | |
| Transmitance to 460 nm | 14.40 | 18.40 | 19.30 |

The following definitions apply:

Firmness is the fruit's resistance to penetration measured in Kilograms (Kg). The measure given has been obtained by the penetrometer ROZE Mod. Arbelette, with a 50 $mm^2$ section head.

Dry Matter is the weight of the residual left from the trituration of the fruit after the drying process at a temperature of 103° C.+2° C. until reaching constant weight.

(%) Dry Matter=Weight Dry Matter/Weight Fresh Matter×100

Humidity & Volatile Matter represents the content in volatile matters and water of the fruits.

(%) Humidity & Volatile Matter=100−% Dry Matter

Maturity Index is the relation between soluble solids and acidity as anhydride citric.

Maturity Index=Soluble solids/Acidity as Anhydride Citric

DETAILED DESCRIPTION OF THE NEW VARIETY

The following additional information is provided to further describe the new variety.

Plant:
- *Habit*.—Upright.
- *Density*.—Medium.
- *Vigor*.—Medium.
- *Height*.—Medium, about 26 cm.
- *Width*.—Medium, about 22 cm.

Leaf:
- *Upperside color*.—About RHS Green group color (near 139B to 139A).
- *Underside color*.—About RHS Yellow-Green group color (near 144A to 146D).
- *Length*.—Approximately 26 cm.
- *Width*.—Approximately 16.5 cm.
- *Shape in cross section*.—Concave.
- *Leaf surface undulation or blistering*.—Absent or Weak.
- *Number of leaflets*.—Three only.
- *Variegation*.—Absent.
- *Glossiness*.—Medium.

Leaf stem characteristics:
- *Color*.—About RHS Yellow-Green group (near 144C to 144B).
- *Position of hairs*.—Slightly outwards.
- *Length*.—Long, approximately 21.0 cm to 22.0 cm.

Terminal leaflet:
- *Length/width ratio*.—Moderately longer.
- *Length*.—Long, approximately 9.0 cm to 9.5 cm.
- *Width*.—Medium, approximately 7.5 cm to 8.0 cm.
- *Shape in cross section*.—Concave.
- *Shape of base*.—Acute.
- *Margin*.—Serrate to crenate.
- *Apex shape*.—Rounded.

Petiole:
- *Attitude of hairs*.—Upwards.
- *Color*.—About RHS Yellow-Green group (near 144C to 144B).
- *Length*.—Long, about 21.0 to 22.0 cm.

Stipule:
- *Anthocyanin coloration*.—Absent or very weak, about RHS Yellow-Green group coloration (near 145D to 145C).
- *Length*.—Medium, approximately 2.5 to 3.0 cm.

Stolons:
- *Number*.—Medium, about 10.
- *Length*.—Medium, approximately 30 cm to 35 cm.
- *Thickness*.—Medium, approximately 3.5 mm to 4.0 mm.
- *Pubescence density*.—Medium.
- *Color*.—About RHS Yellow-Green group (near 144C to 144B).
- *Anthocyanin coloration*.—Absent or very weak, RHS Yellow-Green group coloration (near 144D to 144C).

Inflorescence:
- *Position relative to foliage*.—Same level.
- *Number of flowers*.—Medium, about 6 to 8.

Pedicel:
- *Position of hairs*.—Slightly outwards.
- *Average length*.—Approximately 16.0 cm to 16.5 cm.
- *Average diameter*.—Approximately 2.9 mm to 3.3 mm.
- *Color*.—About RHS Yellow-Green group (near 145C to 145B).

Flower:
- *Medium*.—Medium.
- *Size of calyx relative to corolla*.—Larger.
- *Arrangement of petals*.—Overlapping.
- *Diameter primary flowers*.—Long, approximately 2.6 cm to 3.0 cm.
- *Diameter secondary flowers*.—Medium, approximately 2.1 cm to 2.5 cm.
- *Number of petals*.—About 7-8.
- *Fragrance*.—No significant fragrance.
- *Time from bloom to mature fruit* (*in Huelva, Spain*).—Approximately 30 to 35 days.
- *Stamens*.—Present and numerous with pollen present, fertile and abundant. Length: Approximately 3.5-3.7 mm. Color: About RHS White group (near 155D to 155C).
- *Anthers*.—Generally average in size. Color: About RHS Yellow group (near 12C to 12B) and darkening with advanced maturity.
- *Pollen*.—Fertile and abundant. Color: About RHS Yellow-Orange group (near 16C to 16B).
- *Pistils*.—Abundant.
- *Size*.—Medium.
- *Color*.—About RHS Yellow group (near 13C to 13B).

Petal:
- *Length/width ratio*.—Moderately longer.
- *Length*.—Approximately 10 mm to 13 mm.
- *Width*.—Approximately 8 mm to 10 mm.
- *Shape*.—Cordate to Rounded.
- *Color*.—About RHS White group (near 155C to 155B).
- *Shape of base*.—Obtuse and get narrower.
- *Shape of apex*.—Rounded.
- *Petal margin*.—Glabrous.

Sepal:
- *Attitude of sepals*.—Upwards and outwards.
- *Diameter of calyx in relation to diameter of fruit*.—Slightly larger. Calyx: presents 7 to 9 sepals with lanceolate shape and 3 to 4 smaller sepals with pointed shape.
- *Color upperside of sepals*.—About RHS Green group (near 141 B to 141A).
- *Color underside of sepals*.—About RHS Yellow-Green group (near 143B to 143A).
- *Length of sepals*.—Long, approximately 16 mm to 20 mm.
- *Width of sepals*.—Long, approximately 7 mm to 9 mm.
- *Margin type of sepal*.—Smooth.
- *Apex shape*.—Ovate to acuminate.

*Base shape*.—Straight to get narrower.
*Adherence of calyx*.—Strong.

Fruit:

*Ratio of length/maximum width*.—Moderately longer.
*Color*.—About RHS Red group (near 44B to 44A).
*Peduncle length of inflorescence stem of primary fruit*. About 17 cm to 19 cm.
*Peduncle length of inflorescence stem of secondary fruit*. About 13 cm to 15 cm.
*Peduncle of inflorescence stem color*.—About RHS Yellow-Green group (near 144D to 144C).
*Length primary fruit*.—Long, approximately 5.5 cm to 5.9 cm.
*Width primary fruit*.—Medium, approximately 4.1 cm to 4.6 cm.
*Length secondary fruit*.—Long, approximately 4.6 cm to 5.0 cm.
*Width secondary fruit*.—Medium, approximately 3.4 cm to 3.8 cm.
*Size*.—Medium.
*Shape*.—Conical.
*Difference in shapes between primary and secondary fruits*.—Slight.
*Band without achenes*.—Absent or very narrow.
*Color of achenes*.—About RHS Orange to Orange-Red group (near 44D to 44C).
*Evenness of surface*.—Even or very slightly uneven.
*Evenness of color*.—Even or very slightly uneven.
*Glossiness*.—Medium.
*Position of achenes*.—Below surface.
*Insertion of calyx*.—Level with fruit.
*Firmness*.—Firm.
*Color of flesh*.—About RHS Red group (near 43B to 44C), lightening towards the center.
*Distribution of red color of flesh*.—Marginal.
*Hollow center*.—Absent or small.
*Color of core*.—About RHS Red group (near 41C to 41B).
*Sweetness*.—Medium, approximately 7.50 ° Brix.
*Acidity*.—Medium, approximately 0.55%.
*Time of flowering* (50% *of plants at first flower*).—Early.
*Time of ripening* (50% *of plants with ripe fruits*).—Early.
*Type of bearing*.—Not remontant.
*Chilling*.—Weak.
*Planting date*.—October 14.
10% *flowering*.—November 20.
*First mature fruits*.—December 20.
*Maturity* (15-20 *gms/plant*).—January 15.

Fruiting truss:

*Attitude*.—Semi-erect.

General:

*Planting date*.—October 14.
10% *flowering*.—November 20.
*First mature fruits*.—December 20.
*Maturity* (15-20 *gms/plant*).—January 15.
*Date of planting*.—October 14 in Cartaya (Huelva), Spain, about 7° W, 37° N, and 45 feet elevation.
*Time of flowering*.—10% flowering occurs about November 20 with first mature fruit about December 20 and maturity (15-20 g/plant) about January 15.
*Time of flowers* (50% *of plants at first flower*).—About December 1. Time of ripening (50% of plants with ripe fruit) is about January 5. First mature fruit is about December 20 and maturity (15-20 gms/plant) is about January 15.

Storage qualities:

*Shipping quality*.—Fruits of 'Plared 1075' maintain their quality characteristics when shipped in frigo conditions at temperatures about 2° Centigrade during 60 hours.
*Fruit storage life of 'Plared* 1075' *is medium*.—6 to 8 days at temperatures about 4 to 5° Centigrade.
*Fruit market use*.—Fruits of 'Plared 1075' are suitable for consumption as fresh fruit. Also, they are amenable to processing.
*Time of ripening*.—After planting as aforesaid, plants are grown in raised beds covered with plastic and with small holes in the plastic walls, creating a tunnel. Water and fertilizer were applied through drip irrigation. Time of ripening (50% of plants with ripe fruit) is about January 5. First mature fruit is about December 20 and maturity (15-20 gms/plant) is about January 15.

Disease resistance: No particular sensitivity to any disease or parasite has been observed for 'Plared 1075'.

I claim:

1. A new and distinct strawberry plant as shown and described herein.

* * * * *